(12) United States Patent
Fillion et al.

(10) Patent No.: US 6,713,443 B1
(45) Date of Patent: Mar. 30, 2004

(54) COMPOUNDS WHICH MODIFY SEROTONINERGIC TRANSMISSION, DIAGNOSTIC AND THERAPEUTIC APPLICATIONS

(75) Inventors: Gilles Fillion, Chaville (FR); Jean-Claude Rouselle, Drancy (FR); Olivier Massot, Champigny sur Marne (FR)

(73) Assignee: Institut Pasteur (FR)

( * ) Notice: Subject to any disclaimer, the term of this patent is extended or adjusted under 35 U.S.C. 154(b) by 0 days.

(21) Appl. No.: 08/624,618

(22) PCT Filed: Oct. 4, 1994

(86) PCT No.: PCT/FR94/01158

§ 371 (c)(1),
(2), (4) Date: Jul. 5, 1996

(87) PCT Pub. No.: WO95/09868

PCT Pub. Date: Apr. 13, 1995

(30) Foreign Application Priority Data

Oct. 4, 1993 (FR) ............................................. 93 11804
Jun. 9, 1994 (FR) ............................................. 94 07078
Jun. 9, 1994 (FR) ............................................. 94 07079

(51) Int. Cl.[7] .......................... A61K 38/00; C07K 7/00; C07K 5/02; G01N 33/53
(52) U.S. Cl. ............................ 514/2; 514/18; 530/300; 530/323; 530/345; 435/7.1
(58) Field of Search .................... 514/2, 12, 15–19; 530/300, 327–331, 332, 333, 345; 435/7.1

(56) References Cited

U.S. PATENT DOCUMENTS 5,104,854 A * 4/1992 Schlesinger et al.

FOREIGN PATENT DOCUMENTS

| EP | 0017485 | 10/1980 |
| EP | 280 474 | * 8/1988 |
| EP | 0366638 | 5/1990 |
| FR | PCT/FR91000085 | 2/1991 |

OTHER PUBLICATIONS

Rudinger, In *Peptide Hormones*, ed.J.A. Parsons, University Park Press, Baltimore, pp. 1–7, 1976.*
Pharmacological Reviews, vol. 44,No. 3, 9/92.
Biochemistry & Biophysics, vol. 276, No. 2, Jan. 1, 1990.
Derwent Abstracts 75–56264W (34) 1 page.
Derwent Abstracts 92–076744 (10) 1 page.

* cited by examiner

*Primary Examiner*—Elizabeth Kemmerer
*Assistant Examiner*—Sandra Wegert
(74) *Attorney, Agent, or Firm*—Muserlian, Lucas and Mercanti

(57) ABSTRACT

Compounds having the following peptide sequence: X Leu Y, wherein X is H or Ala or Leu-Ser-Ala, Y is OH or peptide sequence having from 1 to 10 amino acids, with the terminal carboxy end being amidified by a $NH_2$ group, or esterified by a substituted or non-substituted hydrocarbyloxy, with the proviso that X and Y are not simultaneously H and OH, respectively, The invention also concerns the corresponding compounds wherein the peptide binding group —CO—NH— is replaced by a binding group resisting protease enzymatic degradation, or wherein the peptide backbone comprises one or more intercalated groups making the peptide binding resistant to enzymatic degradation. Also described are compounds comprising a grouping whose spatial structure is substantially identical to that of a peptide of the sequence X-Leu-Y wherein X and Y have the above-mentioned definition.

6 Claims, 3 Drawing Sheets

COMPOUNDS WHICH MODIFY SEROTONINERGIC TRANSMISSION, DIAGNOSTIC AND THERAPEUTIC APPLICATIONS

This application is a 371 of PCT/FR94/01158 filed Oct. 4, 1994.

The subject of the present invention is compounds having the property of modifying serotoninergic transmission as well as the diagnostic and therapeutic applications of these compounds.

The cerebral serotoninergic system is a cerebral and peripheral neurotransmission system which uses serotonin or 5-hydroxytryptamine (5-HT) which was discovered during the course of 1949/50.

At the central level, this system is special in that it is extremely centralized (all the cellular bodies are located in the posterior region of the brain, the raphe) and where it projects into practically all the regions of the brain. It is characterized by an extremely high level of varicosity (or equivalent of neuronal ends) along the axons; this arrangement multiplies its points of interaction with the other cerebral neuronal systems. Furthermore, a very large part of this varicosity does not exhibit any synaptic profile, that is to say that the 5-HT released by these "ends" will diffuse and reach the targets (receptors) located at a certain distance; this mechanism requires the use of special receptors having a high affinity for the amine. This structural arrangement is quite favourable for a function of controlling the entire neuronal cells of the brain, and consequently for an essential role in maintaining the homeostasis of the central nervous system.

To exert this control, the 5-HT system uses a large variety of specific receptors. Several families are indeed involved some of which are well characterized ($5\text{-HT}_1$, $5\text{-HT}_2$, $5\text{-HT}_3$, $5\text{-HT}_4$) and others identified more recently are still not well known ($5\text{-HT}_5$, $5\text{-HT}_6$, $5\text{-HT}_7$). Some of them are represented by numerous subtypes; such is the case in particular for the $5\text{-HT}_1^-$ family, characterized by a nanomolar affinity of 5-HT for these sites, and which comprises the subtypes $5\text{-HT}_{1A,B,D,E,F}$.

The $5\text{-HT}_{1B}$ and $5\text{-HT}_{1D}$ type receptors are located on the serotoninergic and non-serotoninergic ends where they modulate the release of the neurotransmitter contained in these ends, in particular they can regulate the release of 5-HT itself (autoreceptors) and play, in this case, a decisive role in the activity of the serotoninergic neurotransmission.

From a fundamental point of view, the serotoninergic system is involved in numerous physiological functions and in numerous pathologies, and especially in depressive syndrome.

Depression is a psychiatric disorder which is still poorly known in spite of numerous studies which have been devoted to it. However, it is now quite clear that most, if not all, depressions involve the serotoninergic system and, especially, it is generally accepted that there is a relationship between a serotoninergic deficiency and suicide.

In addition, antidepressant drugs interact, for a large number of them, with the serotoninergic system and the most recent, which are the most effective and which possess the least undesirable effects, are most often of the "serotoninergic" type. These substances all result, by various mechanisms, in facilitating serotoninergic transmission (inhibitors of monoamine oxidases, inhibitors of recapture, $5\text{-HT}_{1A}$ agonists). However, on the one hand, their efficacy is limited and, on the other hand, they still possess, for many of them, substantial side effects, and finally, their delayed action is substantial (>2 weeks).

Recent results in the literature and from the inventors indicate that the $5\text{-HT}_{1B/1D}$ receptors might play a major role in the depressive syndrome and in the mechanism of action of antidepressants. It has indeed been shown that they not only modulate the liberation of acetylcholine, but they also modulate that of 5-HT itself and thereby effectively regulate the serotoninergic transmission of which the importance in the depressive syndrome is known. Furthermore, they are the target of antidepressants which interact probably in a noncompetitive manner; in other words, the antidepressants are thought to recognize a separate site of the $5\text{-HT}_{1B/1D}$ receptors, but closely interactive with the latter.

The work of the inventors has allowed the identification of a cerebral endogenous compound which recognizes a receptor site capable of interacting with the functioning of certain 5-HT receptors, in particular the $5\text{-HT}_{1B/1D}$ receptors which modulate the release of 5-HT itself.

The cerebral endogenous compound identified is a tetrapeptide of sequence:

Leu-Ser-Ala-Leu (sequence LSAL SEQ ID NO:4).

The inventors also tested the activity of peptides comprising part of the LSAL sequence or the modified LSAL sequence and showed that these compounds still had a good activity on the $5\text{-HT}_{1B/1D}$ receptors. In general, a modification (for example an acetylation) of the $NH_2$-terminal end leads to a compound having a lower ligand activity on the 5-HT receptor, whereas modifications of the COOH end make it possible to obtain a peptide which still has a substantial activity.

For example, the addition of the sequence Gly-Gly-Gly-Tyr to the COOH end of the LSAL sequence makes it possible to obtain a compound still having a substantial activity. However, the addition of the same sequence, but whose Tyr residue is iodinated, leads to a compound no longer having a ligand activity for the 5-HT receptor, probably because of the steric hindrance due to the large size of the iodine atoms which prevent the binding of the peptide thus modified to its receptor.

The subject of the invention is thus a compound of peptide sequence

X Leu Y in which X represents H (SEQ ID NO:1) or Ala (SEQ ID NO:2) or Leu-Ser-Ala (SEQ ID NO:3), Y represents OR, or a peptide sequence having from 1 to 10 amino acids, whose carboxy-terminal end is amidated by an $NH_2$ group or esterified by a substituted or unsubstituted hydroxycarbyloxy residue, with the proviso that X and Y do not simultaneously represent H and OH, respectively as well as the corresponding compounds in which the peptide bonding group —CO—NH— is replaced by a bonding group resistant to the enzymatic degradation of proteases, or in which the peptide backbone comprises one or more intercalated groups making the peptide bond resistant to enzymatic degradation.

Thus, the peptide bonding group (—CO—NH—) is advantageously replaced by a bonding group —CO—NR'—, —$CR_1R_2$—$CR_3R_4$—, —CO—$CR_1R_2$—, $R_1$, $R_2$, $R_3$ and $R_4$, which are identical or different, representing H or a $C_1$–$C_6$ alkyl group, especially a methyl group, and R' representing a $C_1$–$C_6$ alkyl group.

Among the groups which can be intercalated into the peptide backbone, the following groups may be mentioned —$CR_1R_2$—, —$NR_1$— and —O—, $R_1$ and $R_2$ being defined as above.

Hydroxycarbyloxy residue is understood to mean especially an alkyloxy, alkenyloxy or alkynyloxy group, with a linear or branched chain, having from 1 to 10 carbon atoms, unsubstituted or substituted by one or more groups selected from OH, $NH_2$, $NO_2$, Cl, Br, F, $CF_3$ for example the group $OCH_3$, $OC_2H_5$, $OCHOH—CH_3$, $OCHOH—CH_2OH$, $OCH_2CH_2NH_2$, $OC_3H_7$ and the like.

The subject of the invention is more particularly a compound of the following peptide sequence:

Leu-Ser-Ala-Leu-Z (SEQ ID NO:3)

in which Z represents OH, $NH_2$ a substituted or unsubstituted hydrocarbyloxy residue, or a peptide sequence having from 1 to 10 amino acids, as well as the corresponding compounds in which the peptide bond is replaced by a bond resistant to the enzymatic degradation by proteases or in which the peptide backbone comprises one or more intercalated groups making the peptide bond resistant to enzymatic degradation.

The nature of the amino acids of Z is unimportant, the limit being that when modified amino acids are involved (not encoded genetically), these are not substituted by a bulky group (having a size greater than that of the radius of the iodine atom).

The compounds according to the invention comprise especially the peptides of the following sequence:

Ala-Leu;
Leu-Ser;
Ala-Leu-Ser;
Leu-Ser-Ala-Leu (SEQ ID NO:4);
Leu-Ser-Ala-Leu-$OCH_3$ (SEQ ID NO:4);
Leu-Ser-Ala-Leu-$NH_2$ (SEQ ID NO:4);
Leu-Ser-Ala-Leu-Gly-Gly-Gly-Tyr (SEQ ID NO:5);

as well as the analogous compounds in which the peptide bond is replaced by a bond as defined above; or whose backbone comprises an intercalated group as defined above.

The most active compounds are those whose constituent amino acids are in the L form, that is to say the natural form for the peptide structures defined above.

The compounds according to the invention are prepared by extraction from freeze-dried brain as described below or more advantageously by conventional peptide synthesis, for example by the solid-phase method of MERRIFIELD when they are exclusively of peptide nature, or alternatively by modification of the terminal groups of the amino acids and condensation of the residues thus obtained, the reactive functional groups other than those engaged in the bonding between the successive residues having been previously protected with the aid of protecting groups well known to a person skilled in the art.

According to one example of preparation of a peptide according to the invention, the first residue of the COOH terminal end whose amine functional group is protected by a tert-butyloxycarbonyl group is attached to a resin, via its carboxyl group, then, after deprotecting the amine functional group by washing the resin with trifluoroacetic acid in dichloromethane, the second amino acid residue whose amino functional group is protected as above is coupled in dimethylformamide; the amino acid residues which will constitute the peptide portion according to the invention are thus attached one after the other. After deprotection, the amine functional group of the N-terminal residue can be acetylated by the action of excess acetic anhydride in the presence of diisopropylethylamine.

The reactive side chains of the amino acids can be protected for example by a benzyl group, for the hydroxyl side chains.

After removing the protecting group, the peptide according to the invention is removed from the solid support, for example with hydrofluoric acid. The crude product is freeze-dried and subjected to liquid chromatography at moderate pressure, which makes it possible to obtain a practically pure product; the latter is then characterized by high-performance liquid chromatography as well as by analysing its amino acid composition and by mass spectrometry.

The peptides characterized possess the property of modifying serotoninergic transmission through its interactions with the autoreceptors (and also the hetero-receptors) and play a key role in various psychiatric pathologies where the 5-HT system is notoriously involved (stress, anxiety, depression, compulsive obsessions, appetite disorders, sleep disorders, behavioural disorders, aggressiveness and the like).

The subject of the invention is also a compound capable of acting as ligand for the receptor to which the endogenous peptide of sequence Lou-Ser-Ala-Leu (LSAL: SEQ ID NO:4) attaches, characterized in that it comprises a group whose spatial structure is substantially identical to that of a peptide of sequence X-Leu-Y in which X and Y are as defined above, X and Y not simultaneously representing H and OR, respectively.

Such a compound may be an agonist or an antagonist of the peptide LSAL.

"Substantially identical spatial" structure is understood to mean for the purposes of the present invention that the mean position of the atoms forming the group which binds to the receptor only differ at most by 5%, and preferably at most by 2% from the mean position of the atoms forming the corresponding peptide.

Among the preferred compounds, there may be mentioned those comprising a group whose spatial structure is substantially identical to the following di-, tri- and tetrapeptides:

Ala-Leu
Leu-Ser
Ala-Leu-Ser
Leu-Ser-Ala-Leu (SEQ ID NO:4).

The compounds according to the invention are produced from the spatial structures(s) of the peptides according to the invention by computer modelling and conventional chemical synthesis using the structure obtained after modelling, as described in J. Med. Chem., vol. 37, No. 9, pp. 1233 to 1251 and J. Med. Chem., vol. 37, No. 10, pp. 1385–1401.

Advantageously, these compounds are produced, in addition, based on the spatial structure of known antidepressant molecules active on this same site.

The modelling technique makes it possible in particular to define and characterize the structure of molecules not affecting the sites of transport of amines (contrary to most currently known antidepressants) but affecting the unique allosteric site carried by the $5\text{-HT}_{1B/D}$ receptors.

The subject of the invention is also a therapeutic composition comprising a compound as defined above, capable of crossing the haematoencephalic barrier.

To cross the hematoencephalic barrier, the peptide is preferably administered in the form of a prodrug, especially of the glycosyl phosphotriester type, in which the peptide is bound for example through the leucine to the phosphate group, as described in J. MED. CHEM. 92, Vol. 35, p. 30–39.

Such a prodrug, as well as in general a precursor molecule capable of releasing in vivo a compound according to the invention, constitutes another subject of the invention.

The therapeutic composition is advantageously used in pathologies in which the serotoninergic system is involved, especially in the pathologies linked to a deficiency of the serotoninergic transmission.

Thus, the composition according to the invention can be used in particular in the treatment of depression, but also in all the indications currently covered by the antidepressants, such as compulsive obsessional disorders, generalized anxiety, panic attack, appetite disorders, sleep disorders, impulsivity, sexual disorders, aggressivity, and more generally those for the compounds which facilitate serotoninergic transmission.

The composition according to the invention is advantageously provided in an injectable or oral form or in any other known pharmaceutical form.

The effective therapeutic dose is easily determined by a person skilled in the art depending on the nature and the seriousness of the pathology to be treated, as well as the weight and age of the patient. The compounds according to the invention are not toxic. They are added to a pharmaceutically acceptable vehicle or to an excipient well known to a person skilled in the art.

The subject of the invention is also a process for the in vitro diagnosis of a condition linked to the serotoninergic system in a patient, characterized in that a peptide of sequence Leu-Ser-Ala-Leu (SEQ ID NO:4)

is assayed in a biological fluid from the patient.

The assay is carried out especially by an immunological method comprising the bringing of the biological sample into contact with an antibody specifically directed against a peptide according to the invention and the detection of the antigen-antibody complex thus formed.

These processes may be based on a radio-imunological method of the RIA, RIPA or IRMA type, or on an immunoenzymatic method, for example of the ELISA type.

The biological fluid may be blood, urine or the spinal fluid.

The antibodies may be monoclonal or polyclonal and constitute, as well as their Fab, Fab', F(ab')$_2$ and Fc fragments, another subject of the invention.

The antibodies are obtained by coupling a peptide according to the invention to an immunogenic carrier peptide or protein.

The subject of the invention is also a diagnostic kit for assaying a peptide according to the invention in a body fluid from a patient in whom a pathology linked to a deficiency in serotoninergic transmission, especially a masked depression, is suspected, comprising at least one antibody as defined above and optionally the reagents for carrying out the assay.

The peptides of the invention have proved to be inactive on the site of recapture of 5-HT.

The existence of a cerebral endogenous factor not active on the site of recapture constitutes a reference standard in terms of activity and thus makes it possible to envisage a process for the selection of antidepressant substances, consisting in discriminating between the recapture effect and the interaction effect on the 5-HT$_{1B/1D}$ site.

This process applies to known antidepressants and also allows the development of new drugs.

In practice, the discrimination between the recapture effect and the effect on the 5-HT$_{1B/1D}$ site can be carried out by performing tests of inhibition of binding between, on the one hand, increasing quantities of antidepressants and the capture of 5-HT in the synaptosomes, the 5-HT being radiolabelled and, on the other hand, by performing tests of the same type on the 5-HT$_{1B/1D}$ receptor by varying the quantity of antidepressants in the presence of a radiolabelled ligand specific for these receptors, and by determining the respective Ki values or more generally the IC$_{50}$ values.

The choice of antidepressants having a selective activity on the 5-HT$_{1B/1D}$ site will be dictated by the substances having a high Ki or a low IC$_{50}$ in the recapture test and conversely a low Ki or a high IC$_{50}$ in the test of inhibition of binding to the peptide recognition site of the 5-HT$_{1B/1D}$. The radiolabelled (tritium) peptide can also and more easily be used to identify and characterize the specific site for recognition of the peptide, and thus directly to study the capacities of various substances to displace (competition) this peptide by measuring their Ki and by comparing the latter with the Ki values obtained for these same substances to inhibit the capture of 5-HT (or displace a recapture inhibitor, $^3$H-paroxetine for example).

Another subject of the invention also consists in a process for the detection of ligands of the 5-HT$_{1B/1D}$ receptor site for the peptide LSAL, characterized in that there are carried out the steps consisting in:

bringing a molecule or a mixture containing various molecules, optionally not identified, into contact with a recombinant cell expressing the 5-HT$_{1B/1D}$ receptor at its surface, in the presence of a compound according to the invention under conditions allowing the interaction between the 5-HT$_{1B/1D}$ receptor and the said molecule (s), in the case where the latter might have an affinity for the 5-HT$_{1B/1D}$ receptor;

detecting the quantity of the said compound according to the invention bound to the receptor;

deducing therefrom the possible attachment of the said molecule(s).

This process can be used for the detection of agonists or antagonists of the peptide LSAL.

Another subject of the invention relates to a process for the detection of modulators (antagonists or agonists) of the 5-HT$_{1B/1D}$ receptor site for the peptide LSAL characterized in that there are carried out the steps consisting in:

bringing a molecule or a mixture containing various molecules, optionally not identified, into contact with a recombinant cell expressing the 5-HT$_{1B/1D}$ receptor at its surface, in the presence of a compound according to the invention under conditions allowing the interaction between the 5-HT$_{1B/1D}$ receptor and the said compound according to the invention;

detecting the molecules capable of mimicking or antagonizing the activity of the compound according to the invention on the said receptor.

Ligands obtained according to a process as described above can be used as active ingredient of a therapeutic composition useful in the treatment of psychiatric disorders such as depression, circulatory disorders such as migraine, or immunological disorders linked to the 5-HT$_{1B/1D}$ receptors.

The compounds according to the invention are also useful as diagnostic tools for labelling the 5-HT$_{1B/1D}$ receptors, and more particularly the endogenous peptide binding site on these receptors.

To this end, a diagnostic composition comprising a radiolabelled compound according to the invention is advantageously used in an imaging technique using a positon emission tomography scanner.

The isolation and the characterization of the peptide Leu-Ser-Ala-Leu (SEQ ID NO:4) according to the invention, as well as the binding properties and the pharmacological activities on the 5-$HT_{1B/1D}$ receptors of the peptide Leu-Ser-Ala-Leu will be described below with reference to the accompanying figures in which:

FIG. 1 represents the binding interactions with [$^{125}$I]cyanopindolol.

The binding of [$^{125}$I]cyanopindolol was measured as described in HOYER D. et al., Eur. J. Pharmacol. 118, 1–12 (1985).

FIG. 1A represents the results obtained with rat brain cortical membranes (50 μg of protein), incubated for 60 minutes at 37° C. in a total volume of 100 μl in the presence of 0.3 nM [$^{125}$I]cyanopindolol.

The incubation was carried out in a 5 mM Tris-HCl buffer, pH 7.5, containing 154 mM NaCl, 1 μM pargyline, 30 μM isoproterenol and various concentrations of the peptide ($10^{-13}$ to $10^{-8}$ M). Each point corresponds to a mean plus or minus the standard deviation of five independent determinations.

FIG. 1B represents the results obtained with membranes of NIH 3T3 cells transfected with the 5-$HT_{1B}$ receptor gene (50 μg of protein), incubated for 60 minutes at 37° C. in the presence of 0.3 nM [$^{125}$I]cyanopindolol. Binding was measured as for FIG. 1A.

FIG. 1C represents the results obtained from rat brain cortical membranes (50 μg of protein) incubated for 60 minutes at 37° C. in a total volume of 100 μl, in the presence of increasing concentrations of [$^{125}$I]cyanopindolol (0.06 to 0.35 nM) with (○) or without (●) the peptide at 1 nM. Each point corresponds to the mean plus or minus the standard deviation of three independent determinations.

NIH 3T3 cell membranes expressing the mouse 5-$HT_{1B}$ receptor gene were suspended and homogenized with a Dounce homogenizer in a 50 mM Tris-HCl buffer, pH 7.4, containing 3 mM $MgCl_2$ and 0.2 mM EGTA (TME buffer).

The adenylyl cyclase activities were measured on aliquot fractions of 50 μl (30–50 μg of protein) of homogenates in a final volume of 100 μl, containing 0.1 mM [α-$^{32}$P]ATP (1 μCi), 1 mM $MgCl_2$, 50 μM GTP, 10 μM forskolin, 100 mM NaCl, 10 mM theophylline, 20 mM phosphocreatinine, 0.2 mg/ml creatine kinase, 1 mM [$^3$H]cAMP (=15,000 cpm/test) and the substances to be studied.

The membranes were incubated for 20 minutes at 30° C. The reaction was stopped by addition of 200 μl of 5 mM ATP, 5 mM cAMP and 1% sodium dodecyl sulphate dissolved in 50 mM Tris-HCl buffer.

The [$^{32}$P]cAMP formed was isolated by the two-column chromatography method described by Salomon et. al. (Adv. Cyclic Nucleotide Res., 10, 35–55 (1979), modified by De Vivo and Maayani (J. Pharmacol. Exp. Therap. 238, 248–253 (1986)).

FIG. 2A expresses the effect of LSAL as a function of its concentration on the enzymatic activity stimulated by forskolin in the presence of 0.1 μM 5-Ht.

FIG. 2B expresses the dose-response curve of the effect of 5-HT on the enzymatic activity stimulated by forskolin in the absence (● ---- ●), or in the presence (○ ---- ○) of LSAL ($10^{-9}$ M).

Figure 3:
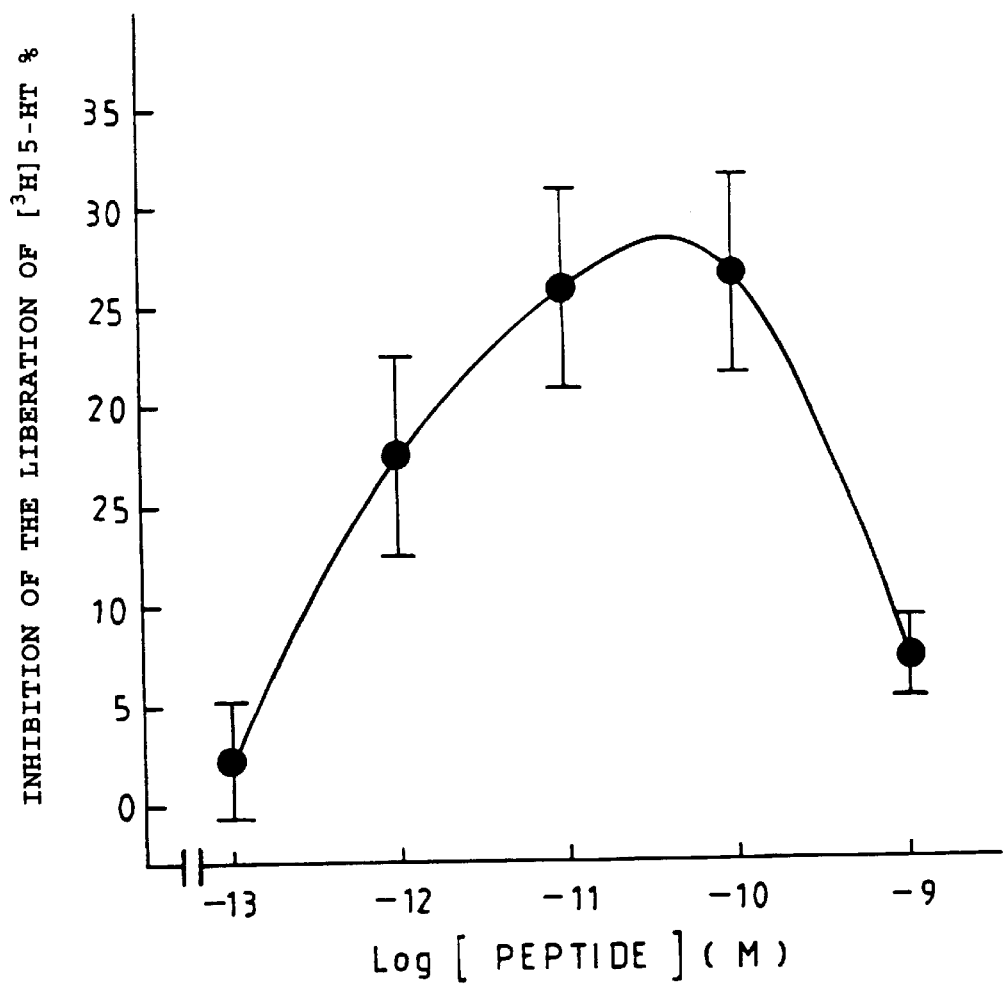

FIG. 3 represents the effect of the peptide on the release of serotonin in the synaptosomes of rat brain hippocampus. The results are expressed in percentages of [$^3$H]5-HT release ($P_2/P_1$ ratio) in the absence of peptide. Each point is the mean plus or minus the standard deviation of triplicate determinations, obtained with the aid of 3–6 separate hippocampus homogenates.

The method used is the method described above (BOLANOS-JIMENEZ B. et al., Eur. J. Pharmacol. 242, 1–6 (1993)) with the following modifications: the [$^3$H] acetylcholine was substituted by 60 nM [$^3$H]5-HT and 0.01% ascorbic acid was added to the incubation medium.

1. Isolation and Purification of the Peptide Leu-Ser-Ala-Leu

Using, as discrimination criterion, the capacity of a potential factor to interact with the recognition of 5-HT by the 5-$HT_{1B/1D}$ receptor of membranes of rat brain synaptosomes, as described in FR-2,657,784, an active compound was purified from rat, horse and bovine brain extracts. The methodology of the purification involved separations by gel permeation, normal or reversed phases or alternatively ion exchanges.

It is summarized in the table below:

Steps for purification of the endogenous peptide

| STEPS OF THE CHROMATOGRAPHY | CONDITIONS FOR THE CHROMATOGRAPHY | ACTIVE FRACTION (Elution or retention time) |
| --- | --- | --- |
| SIZE EXCLUSION (TSK HW 40S, Merck, 600 × 26 mm) | Isocratic elution with a 50 mM ammonium acetate ($CH_3COONH_4$) buffer (pH 5) Flow rate: 2 ml. $min^{-1}$ | $T_R$ = 80 min. |
| REVERSED PHASE ($C_{18}$, Ultrabase, Shandon, 250 × 10 mm) | Linear gradient of elution from A to B for 12 minutes: A: 50 mM $CH_3$ $COONH_4$ (pH 5); B: 50 mM $CH_3$ $COONH_4$ (pH 5)/$CH_3CN$, 88/12 Step gradient for 5 min. with C. C: 50 mM $CH_3COONH_4$ (pH 5)/$CH_3CN$, 50/50 Flow rate: 4 ml. $min^{-1}$ | $T_R$ = 20 min. |
| SIZE EXCLUSION (Sephadex $G_{25}$, Pharmacia, 450 × 16 mm) | Isocratic elution with 10 mM $CH_3COONH_4$ (pH 5) Flow rate: 0.3 ml. $min^{-1}$ | $T_R$ = 240 min. |
| REVERSED PHASE | Linear gradient of elution from A | $T_R$ = 5.75 min. |

-continued

Steps for purification of the endogenous peptide

| STEPS OF THE CHROMATOGRAPHY | CONDITIONS FOR THE CHROMATOGRAPHY | ACTIVE FRACTION (Elution or retention time) |
|---|---|---|
| ($C_{18}$, Ultrabase, Shandon, 250 × 10 mm) | to B for 15 minutes: A: 50 mM $CH_3COONH_4$ (pH 5)/$CH_3CN$, 85/15 B: 50 mM $CH_3COONH_4$ (pH 5)/$CN_3CN$, 75/25 Step gradient for 5 min. with C. C: 50 mM $CH_3COONH_4$ (pH 5)/$CN_3CN$, 50/50 Flow rate: 4 ml. $min^{-1}$ | |
| REVERSED PHASE ($C_{18}$, Ultrabase, Shandon, 250 × 10 mm) | Linear gradient of elution from A to B for 35 minutes: A: 50 mM $CH_3COONH_4$ (pH 5); B: 50 mM $CH_3COONH_4$ (pH 5)/$CH_3CN$, 70/30 Flow rate: 4 ml. $min^{-1}$ | $T_R$ = 28 min. |
| PSEUDOREVERSED PHASE (Charcoal column, hypercarb., Shandon, 100 × 3 mm) | Linear gradient of elution from A to B for 30 minutes: A: 50 mM $CH_3COONH_4$ (pH 5); B: 50 mM $CH_3COONH_4$ (pH 5)/$CH_3CH$, 70/30 Flow rate: 1 ml. $min^{-1}$ | $T_R$ = 12.71 min |
| REVERSED PHASE ($C_{18}$, Ultrabase, Shandon, 150 × 4 mm) | Isocratic elution with 0.05% TFA/$CH_3CN$, 83/17 Flow rate: 1 ml. $min^{-1}$ | $T_R$ = 5.14 min |

The characterization of the fractions obtained was performed essentially on the basis of NMR analysis, amino acid analysis and amino acid sequencing. The purified compound consisted of Leu-Ser-Ala-Leu.

The same fraction was also obtained from horse and bovine brain, which means that this peptide is conserved in mammals.

2. Interactions of the Purified Peptide with the $5\text{-}HT_{1B/1D}$ Receptors The synthetic peptide LSAL was tested for its capacity to "mimic" the effects of the purified fraction obtained from brain extracts. LSAL inhibits the binding of [$^3$H]5-HT to the $5\text{-}HT_1$ receptors with an $IC_{50}$ of close to $10^{-11}$M and a maximum inhibitory effect of 30 to 50% occurring at a concentration of $10^{-9}$M. The binding to $5\text{-}HT_{1nonA}$ which, under the experimental conditions used, represents mainly the $5\text{-}HT_{1B/1D}$ sites, is inhibited up to a maximum value of 75%, as represented in Table 2 below with an identical $IC_{50}$.

The latter observation indicates that the $5\text{-}HT_{1B/1D}$ receptors are particularly sensitive to the peptide. Accordingly, tests were carried out on rat cerebral tissue homogenates in which the $5\text{-}HT_{1B}$ receptors were specifically labelled with [$^{125}$I]cyanopindolol, the interaction corresponded to an $IC_{50}$ of $10^{-11}$M and a maximum effect of 60% inhibition, as represented in FIG. 1A.

In addition, the activity of this peptide on the $5\text{-}HT_{1D}$ receptors was demonstrated in guinea pigs and on human brain with the aid of [$^3$H]5-HT. The value of the $IC_{50}$ was again $10^{-11}$M. These results strongly suggest that in vitro, the $5\text{-}HT_{1B/1D}$ receptors constitute the target of the LSAL peptide.

The activity of the peptide was also evaluated on the binding to the $5\text{-}HT_{1B}$ receptors in NIH 3T3 cells transfected with the mouse $5\text{-}HT_{1B}$ receptor gene.

Figure 1:
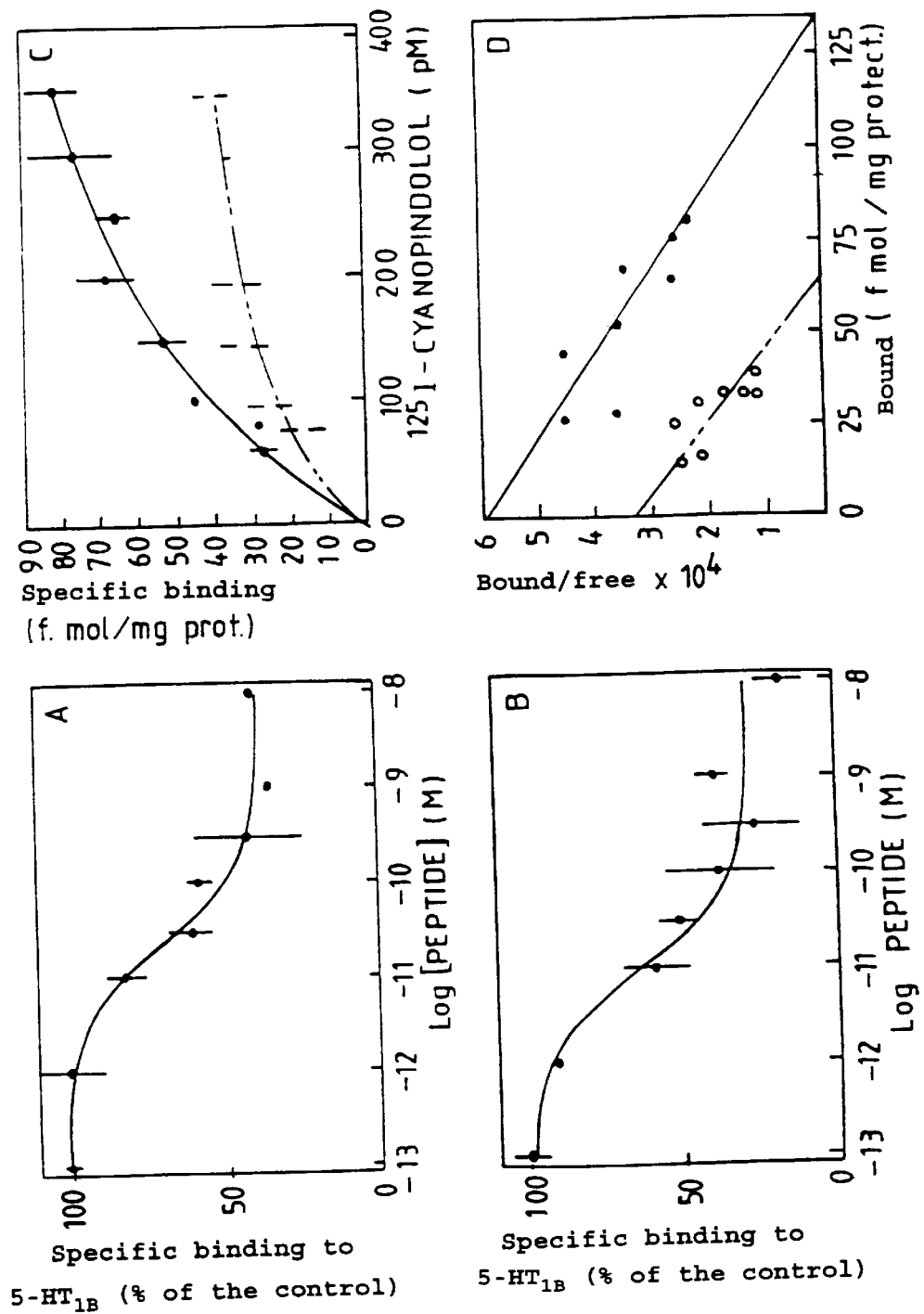
FIG. 1D represents the Scatchard curve of the saturation curves.

The inhibitory effect of the peptide was very similar to that observed in cerebral tissue homogenates (FIG. 1B).

The maximum effect corresponded to 70% inhibition of the specific binding of [$^{125}$I]cyanopindolol with an $IC_{50}$ value of $10^{-11}$M. This result clearly demonstrates that LSAL interacts directly with the $5\text{-}HT_{1B}$ receptors.

To study further the type of interaction of the tetrapeptide with the $5\text{-}HT_{1B/1D}$ receptors, saturation curves for the radiolabelled ligand were established in the presence of the peptide. The binding results obtained suggest that the inhibitory activity of the peptide corresponds to a noncompetitive interaction (FIGS. 1C, 1D).

This result was observed with [$^3$H]5-HT, as well as with [$^{125}$I]cyanopindolol for labelling the $5\text{-}HT_{1B}$ receptors and is in agreement with the preceding hypothesis of the existence of a specific site for the peptide separate from, but closely related to, the 5-HT binding site.

The pharmacological specificity of the partially purified fractions was studied during a subsequent purification using rat brain homogenates. The tests were carried out using the synthetic LSAL to determine if the peptide interacted or not with other 5-HT receptors, or those of other neurotransmitters.

The $5\text{-}HT_{1A}$ receptors were not affected at a concentration of the peptide which strongly antagonized the binding to $5\text{-}HT_{1B/1D}$.

Similarly, the binding of radioligands to the $5\text{-}HT_{1E}$, $5\text{-}HT_{1F}$, $5\text{-}HT_2$ and $5\text{-}HT_3$ receptors was not affected (Table 2), which indicates that, among the serotoninergic receptors studied, only the $5\text{-}HT_{1B/1D}$ class was sensitive to the peptide. The binding of other specific radioligands to various neurotransmitter receptors was examined: the α- and β-adrenergic, dopaminergic muscarinic, histaminergic, opiate and benzodiazepine receptors. The binding to these receptors was not significantly reduced by LSAL at concentrations which had a maximum inhibitory effect for the binding to the $5\text{-}HT_{1B/1D}$ receptors (Table 2).

TABLE 2

Inhibitory effect of the peptide on various radioligand bindings in rat brain tissues

| RECEPTORS | LIGANDS | INHIBITORY EFFECT AS % OF THE CONTROL |
|---|---|---|
| SEROTONINERGIC | | |
| 5-HT$_{1A}$ | [$^3$H]8-OH-DPAT (3 nM) | 0 |
| 5-HT$_{1B}$ | [$^{125}$I]cyanopindolol (0.3 nM) + 30 μM isoproterenol + 0.1 nM 8-OH DPAT | 70 ± 2 |
| 5-HT$_{1\,NON\,A}$ | [$^3$H]5-HT (30 nM) + 0.1 μM 8-OH-DPAT | 75 ± 3 |
| 5-HT$_{1EFC}$ | [$^3$H]5-HT (30 nM) + 20 nM 5-CT | 0 ± 10 |
| 5-HT$_{2A}$ | [$^3$H]ketanserin (5 nM) | 10 ± 5 |
| 5-HT$_{2A}$ | [$^3$H]DOB (5 nM) | 2 ± 8 |
| 5-HT$_3$ | [$^3$H]BRL 43694 (3 nM) | 0 ± 10 |
| ADRENERGIC | | |
| α$_1$ | [$^3$H]prazosin (2 nM) | 5 ± 3 |
| β | [$^3$H]dihydroalprenolol (3 nM) + 5-HT-5 | 10 ± 15 |
| DOPAMINERGIC | | |
| D$_2$ | [$^3$H]epiperone (2 nM) + 10 μM 5-HT | 2 ± 3 |
| HISTAMINERGIC | | |
| H$_1$ | [$^3$H]mepyramine (5 nM) | 10 ± 10 |
| MUSCARINIC | [$^3$H]quinuclidinyl benzilate (3 nM) | 0 ± 2 |
| OPIATE | [$^3$H]naloxone (2 nM) | 10 ± 10 |
| BENZODIAZEPINE | [$^3$H]flunitrazepam (3 nM) | 2 ± 2 |

Legend to Table 2

Rat brain cerebral membranes (200 μg) were incubated for 30 minutes at 25° C. with various specific radioligands (see table) in the presence or in the absence of 1 nM peptide.

The various binding conditions used for the serotoninergic receptors are those described above (PALACIOS J. M. et al., Methods in Neurosciences 12, 238–262 (1993)). For the other bindings, the incubation medium consisted of 50 mM Tris-HCl pH 7.4 containing 120 mM NaCl and 50 mM KCl ([$^3$H]spiroperidol, [$^3$H]quinuclidinyl benzilate, [$^3$H]naloxone, or 4 mM CaCl$_2$ and 4 mM MgCl$_2$ ([$^3$H]flunitrazepam), or 120 mM NaCl, 5 mM KCl, 2.5 mM CaCl$_2$ and 1 mM MgSO$_4$ ([$^3$H]prazosin), or 90 mM NaCl ([$^3$H]dihydroalprenolol).

Each point corresponds to a mean plus or minus the standard deviation of five independent determinations.

The tetrapeptide identified did not show any other effect on the recapture of 5-HT in the synaptosomal preparations. Neither did it show any effect on the recapture of other neurotransmitters (or their precursors), for example choline, GABA, histamine, dopamine and noradrenaline. This result indicates that the peptide is different from the endogenous compounds previously suspected of interacting with the transport of amines.

The binding of [$^3$H]5-HT or of [$^{125}$I]cyanopindolol to the 5-HT$_{1B/1D}$ type receptors is also inhibited by the following peptides with the corresponding IC$_{50}$ values:

Ala-Leu IC$_{50}$=10$^{-6}$ M
Leu-Ser IC$_{50}$=10$^{-5}$ M
Ala-Leu-Ser IC$_{50}$=10$^{-6}$ M

By way of comparison, the peptide Ala-Leu-Leu-Ser proved to be inactive in the only test carried out.

The peptide Ala-Leu is active in its L form (natural form) and exhibits practically no activity in its D form.

The Ala-Leu and Leu-Ser fractions also showed a high specificity of interaction since their inhibitory effect on the binding was exerted only on the 5-HT$_1$ subtypes of the 5-HT receptors and more particularly on the 5-HT$_{1B/1D}$ subtype; under the experimental conditions used, they did not appear to affect the 5-HT$_2$ and 5-HT$_3$ receptors or the α-adrenergic, β-adrenergic, dopaminergic, muscarinic and histaminergic receptors, the benzodiazepine receptors and the opiate receptors. These peptides also lack the activity for displacing the label from the sites of transport ([$^3$H]paroxetine) and are not inhibitors of the recapture of 5-HT.

The activity of the peptide Ala-Leu was, in addition, measured in preliminary tests on the inhibitory function of the 5-HT$_{1B/1D}$ receptors on the evoked release of acetylcholine.

In agreement with the results of the binding studies indicating an interaction with the 5-HT$_{1B/1D}$ receptors, it was shown that the peptide LSAL antagonized the modulatory activity of the 5-HT$_{1B/1D}$ receptors at a very low concentration and, on the contrary, potentiated the effect of a 5-HT$_{1B}$ agonist at a higher concentration. These results as a whole suggest that this peptide could play the role of an allosteric modulator of the 5-HT$_{1B/1D}$ receptor.

3) Interaction of LSAL with the Functional Activity of the 5-HT$_{1B}$ Receptors (Transduction System)

The 5-HT$_{1B/D}$ receptors are known to be predominantly coupled to the Gi protein, inhibiting the activity of adenylyl cyclase. The interaction of LSAL was examined on the enzymatic activity correlated with the 5-HT$_{1B}$ receptor stimulation expressed in NIH 3T3 cells.

Figure 2:
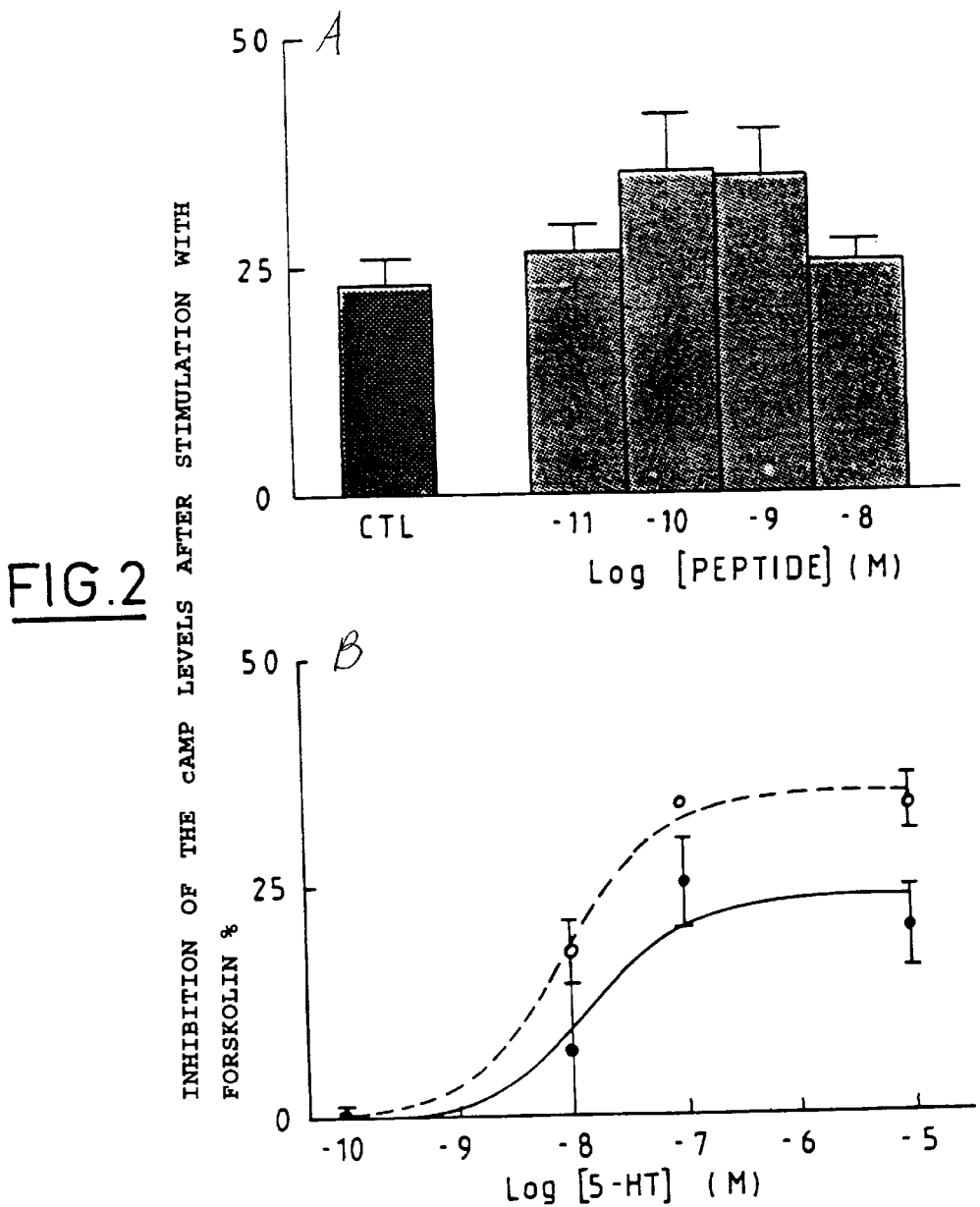
FIG. 2 represents the results of the effects of LSAL on the adenylyl cyclase activity stimulated by forskolin.

The peptide did not have any effect on the basal production of cAMP. However, it significantly increased the inhibitory effect of 5-HT on the adenylyl cyclase activity stimulated by forskolin (FIG. 2). This activity was dependent on the concentration, with a bell-shaped dose-response curve. The activity of the peptide on rat substantia nigra homogenates was practically similar. These results clearly indicate that LSAL interacts with the activity of the 5-HT$_{1B}$ receptor.

4) Effects of the Peptide on the Cellular Functional Activity of the 5-HT$_{1B/D}$ receptors The activity of the peptide on the liberation of [$^3$H]5-HT from rat brain hippocampus synaptosomes previously charged with radioactive amine was examined.

The K$^+$-induced liberation of [$^3$H]5-HT was decreased in the presence of LSAL in a dose-dependent manner with an apparent IC$_{50}$ of close to 10$^{-11}$M. The maximum effect observed at a concentration of 10$^{-10}$M corresponds to a 20 to 25% inhibition of the evoked liberation and decreases at higher concentrations (FIG. 3).

In series of tests of which the conditions are similar to those used for the binding tests (at equilibrium), the peptide LSAL no longer potentiates the action of 5-HT but, on the contrary, counteracts its inhibitory effect on the liberation of [$^3$H]5-HT.

These results demonstrate that LSAL interacts with the cellular function correlated with the activity of the 5-HT$_{1B/1D}$ receptors. The most probable hypothesis to explain these results is that the peptide LSAL which acts as allosteric modulator of the 5-HT$_{1B/1D}$ receptor is capable of inducing conformational transitions of this receptor corresponding either to an active state (potentiation) or to a desensitized state (inhibition) of the receptor.

5) Effects of LSAL in vivo

Tests were carried out in vivo in nice, to examine the behavioural effects of LSAL.

Insofar as previous neuropharmAcological studies had shown the involvement of the 5-HT$_{1B}$ receptors in disorders linked to stress and anxiety, the effects of the peptide were examined in two animal models of anxiety.

Open Field Test

The activity of LSAL was determined in the open field test on c57/black-6 mice. Male C57/BL/6 mice (20–25 g) were used. The open field consisted of a white plastic box (35×35×20 cm) divided into 25 equal squares. LSAL dissolved in 5 ml of 0.9% saline solution in a volume of 5 μl was injected via the icv route into the mice, which were placed in a corner of the box. After two minutes, the number of squares crossed, the U-turns made and the immobilization time were measured. The results are expressed as the mean plus or minus the standard deviation. Difference with the control: *p<0.05, **p<0.005 (student's test). At doses of 50 μg ICV per animal, the exploratory activity was significantly decreased compared with the control animals which received the excipient under the same conditions (Table 3).

TABLE 3

Effect of intracerebroventricular injections of LSAL in mice in the open field test

| Substance injected | Number of animals | Number of squares crossed | Number of rightings | Immobilization time (sec.) |
|---|---|---|---|---|
| Control (NaCl) | 12 | 115 ± 9 | 23 ± 3 | 12 ± 5 |
| LSAL 50 μg | 12 | 88 ± 9* | 15 ± 3* | 47 ± 8** |

Raised Cross-shaped Labyrinth

This experimental test is used to determine the degree of anxiety and consists in a raised labyrinth with two branches, one protected by walls and the other unprotected.

The animal is assumed to be anxious when it avoids the entrance and reduces the time spent in the open branches.

Male BALB/C mice weighing 20 to 24 g were used.

The raised cross-shaped labyrinth was made of plexiglass with open branches and two closed branches of the same size (12.5×5 cm) with walls 15 cm high, these branches extending from a central platform of 5×5 cm, placed 40 cm above the ground.

LSAL dissolved in 5 ml of saline solution at 0.9% in a volume of 5 μl was injected via the icv route into the mice. Three hours later, the animal was placed on the central platform of the labyrinth. Each entry into a branch as well as the time spent in each branch was recorded. The duration of the test was 5 minutes. The labyrinth was cleaned after each test.

LSAL was tested under conditions of low light intensity (BENJAMIN D. et al., Life Sci. 47, 195–203 (1990)).

The results were expressed as mean plus or minus the standard deviation of the percentage of entries into the open branches (% entries into the open branches), percentage of time spent in the open branches (% time in the open branch) and total number of entries into the branches. Difference with the control: *p<0.05, **p<0.01 (student's test).

TABLE 4A (1 hour after i.v. injection)

| Substance injected | Number of animals | % entries into the open branches | % time spent in the open branches | % Total entries into the branches |
|---|---|---|---|---|
| Control (NaCl) | 16 | 77 ± 9 | 74 ± 8 | 5 ± 1 |
| LSAL 0.5 μg | 16 | 63 ± 11 | 64 ± 8 | 8 ± 2 |

TABLE 4A-continued (1 hour after i.v. injection)

| Substance injected | Number of animals | % entries into the open branches | % time spent in the open branches | % Total entries into the branches |
|---|---|---|---|---|
| LSAL 2 μg | 16 | 69 ± 10 | 73 ± 8 | 8 ± 2 |
| LSAL 10 μg | 16 | 80 ± 6 | 69 ± 6 | 9 ± 2* |

TABLE 4B (3 hours after i.v. injection)

| Substance injected | Number of animals | % entries into the open branches | % time spent in the open branches | % Total entries into the branches |
|---|---|---|---|---|
| Control (NaCl) | 35 | 62 ± 5 | 71 ± 5 | 8 ± 1 |
| LSAL 2 μg | 6 | 60 ± 8 | 62 ± 9 | 15 ± 2** |
| LSAL 10 μg | 16 | 80 ± 5** | 85 ± 4* | 14 ± 1** |
| LSAL 50 μg | 26 | 56 ± 7 | 55 ± 7* | 8 ± 1 |

This result strongly suggests that under the experimental conditions used, the peptide has an anxiogenic effect. A dose of 10 μg of LSAL increases the number of entries into the unprotected open branches of the labyrinth, suggesting an anxiolytic effect of this peptide under the test conditions.

Forced Swiming Test

The forced swimming test (Porsolt) is a simple test which cannot, under any circumstances, be assimilated with a model of "depression". It has, however, the merit of discriminating between a good number of antidepressant substances. It should however, be noted that some antidepressants are not active in this test and some non-antidepressant substances are active in it.

Under experimental conditions where the anti-depressant activity is measured in this test, it was shown that the peptide Ala-Leu injected via the ip route at high concentration, but also the i.c.v. (intra cerebroventricular route) at low concentration, reduces slightly but significantly the mouse immobility time; the noradrenergic type (nomifensine) antidepressants are much more effective than the peptide in this test, but the serotoninergic antidepressants also have a weak activity.

The measurement of the horizontal locomotor activity was performed in an activity-measuring apparatus. The peptide has a stimulant effect. During this test, a high increase in defecations (sign linked to anxiety) was noted in the animals who received the peptide.

However, in all these tests, it seems that the initial state of "stress" in the animals plays a role in the extent of the phenomena observed.

Various series of tests were performed on the effects of the dipeptide Ala-Leu on appetite. Administrations via the i.c.v. route of 7 to 30 μg of the peptide have very significant effects on the consumption of food in mice, since they cause, over 24 hours, a decrease of nearly half the food consumed by the animals, as well as a weight loss which is also significant.

The latter observations are indeed in agreement with the fact that the serotoninergic antidepressants most often have major effects on food consumption, some increasing, others reducing weight in the patients treated, and that their activity is exploited in bulimia or anorexia cases which often accompany depression.

These behavioural changes observed after in vivo administration of LSAL and other peptides according to the invention show strongly that the molecular and cellular changes induced by the peptide effectively lead to changes in the function of the central nervous system. Indeed, LSAL seems capable of inducing anxiety after administration in vivo. LSAL appears as an endogenous regulator, capable of finely modulating the control exerted by 5-HT on neurotransmission at the level of the central nervous system. It probably plays a key role in the physio-pathological functions (sleep, thermo-regulation, learning and memory, behaviour, pain and the like), as well as in physio-pathological mechanisms (stress, anxiety, depression, aggressivity, nutritional disorders and the like) known or strongly suspected of involving the serotoninergic system. It should also play a major role in pathologies linked to blood pressure and migraine because $5-HT_1$ type ($5-HT_1$-like (probably $5-HT_D$)) receptors have been located in human brain vessels and in other smooth muscles.

It undoubtedly also regulates the immune response since the $5-HT_{1B/1D}$ receptors are present immuno-competent tissues, and since the transmission of 5-HT is known to interact with the immune response.

7) Relative Activity of the Peptides According to the Invention

The relative activity of different amino acids or peptides at 1 nM was determined on $5-HT_{1B}$ and $5-HT_{1B/1D}$ receptors with the aid of 0.3 nM [$^{125}$I]cyanopindolol and 30 nM [$^3$H]5-HT respectively. The binding experiments were performed as described above. The results are expressed as a percentage of the LSAL effect. Each value corresponds to the mean ± the standard deviation of three independent tests performed in quintuplicate.

TABLE 5

| AMINO ACIDS AND PEPTIDES | RELATIVE POTENCY | |
|---|---|---|
| | Receptors $5-HT_{1B/D}$([$^3$H]5-HT) | Receptors $5-HT_{1B/D}$([$^{125}$I]-cyanopindolol) |
| ALA | 0 ± 4 | 1.7 ± 1.68 |
| LEU | 2 ± 9 | 0 ± 2 |
| SER | 0 ± 5 | 0 ± 1.7 |
| ALA-LEU | 50 ± 5 | 61.5 ± 5 |
| β-ALA-LEU | 0 ± 13 | N.D.* |
| D-ALA-LEU | 0 ± 10 | N.D.* |
| β-ALA-DL-LEU | 2 ± 13 | N.D.* |
| LEU-ALA | 1 ± 2 | 1.7 ± 1.6 |
| LEU-SER | 45.7 ± 7 | 53.8 ± 8 |
| SER-LEU | 4 ± 4 | N.D.* |
| ALA-LEU-SER | 28 ± 10 | 33.8 ± 10 |
| ALA-LEU-LEU-SER (SEQ ID NO:6) | 10 ± 15 | 23.6 ± 10.6 |
| LEU-SER-ALA-LEU (SEQ ID NO:4) | 100 ± 5 | 100 ± 10 |
| AC-LEU-SER-ALA-LEU (SEQ ID NO:4) | 26.7 ± 10 | N.D.* |
| LEU-SER-ALA-LEU-NH$_2$ (SEQ ID NO:4) | 83.3 ± 16 | N.D.* |
| LEU-SER-ALA-LEU-GLY-GLY-GLY-TYR (SEQ ID NO:5) | 80.9 ± 9.5 | N.D.* |

*N.D.: Not Determined

What is claimed is:

1. A peptide capable of modifying serotoninergic transmission having a formula selected from the group consisting of X-Leu-Y, Ala-Leu-Ser and Leu-Ser-Ala-Leu-Z wherein X is selected from the group consisting of hydrogen, and Leu-Ser-Ala, Y is selected from the group consisting of a peptide sequence of 1 to 10 amino acids with a terminal carboxy amidated with —$NH_2$ or esterified with unsubstituted or substituted hydrocarbyloxy, Z is selected from the group consisting of a peptide sequence of 1 to 10 amino acids, —OH, —$NH_2$ and unsubstituted or substituted hydrocarbyloxy, and compounds selected from the group consisting of X-Leu-Y, Ala-Leu-Ser and Leu-Ser-Ala-Leu-Z in which the peptide group —CO—NH— is replaced with a group resistant to enzymatic degradation of proteases or in which the peptide backbone has at least one intercalated group making the peptide bond resistant to enzymatic degradation.

2. A compound of claim 1 wherein the peptide bonding —CONH— is replaced by a member of the group consisting of —CO—, —NR'—, —$CR_1R_2$, —$CR_3R_4$— and —CO—$CR_1$—$R_2$ or in which the peptide backbone has at least one intercalated group selected from the group consisting of —$CR_1R_2$—, —$NR_1$— and —O—, $R_1$, $R_2$, $R_3$ and $R_4$ are individually hydrogen or an alkyl group of 1 to 6 carbon atoms and R' is an alkyl group of 1 to 6 carbon atoms.

3. A compound of claim 1 having the sequence selected from the group consisting of Leu-Ser-Ala-Leu (SEQ ID No: 1), Leu-Ser-Ala-Leu-$OCH_3$ (SEQ ID No: 2), Leu-Ser-Ala-Leu-$NH_2$ (SEQ ID No: 3) and Leu-Ser-Ala-Leu-Gly-Gly-Gly-Tyr (SEQ ID No: 4) and compounds of the same sequence wherein the peptide bond is replaced by a bond resistant to enzymatic degradation by proteases or the peptide backbone has at least one intercalated group making the peptide bond resistant to enzymatic degradation.

4. A compound of claim 1 in the L-form.

5. A diagnostic composition comprising a radiolabelled compound of claim 1 and an inert pharmaceutical carrier.

6. A peptide of claim 1 wherein the hydrocarbyloxy is selected from the group consisting of an unsubstituted or substituted alkoxy group, a alkenyloxy group and an alkylnyloxy group of up to 10 carbon atoms, the substituents being at least one member of the group consisting of —OH, —$NH_2$, —$NO_2$, —$CF_3$, an alkoxy group, an alkoxyhydroxy group and an alkoxyamino group.

* * * * *

SEQUENCE LISTING

<160> NUMBER OF SEQ ID NOS: 4

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: peptide
      designed to modify serotoninergic transmission

<400> SEQUENCE: 1

Leu Ser Ala Leu
  1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: peptide
      designed to modify serotoninergic transmission
<220> FEATURE:
<221> NAME/KEY: MOD_RES
<222> LOCATION: (4)
<223> OTHER INFORMATION: esterified leucine

<400> SEQUENCE: 2

Leu Ser Ala Leu
  1

<210> SEQ ID NO 3
<211> LENGTH: 4
<212> TYPE: PRT

```
-continued

<213> ORGANISM: Artificial Sequence
<220> FEATURE:
<223> OTHER INFORMATION: Description of Artificial Sequence: peptide
      designed to modify serotoninergic transmission
<220> FEATURE:
<221> NAME/KEY: MOD_RES
<222> LOCATION: (4)
<223> OTHER INFORMATION: AMIDATION

<400> SEQUENCE: 3

Leu Ser Ala Leu
  1

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: peptide
      designed to modify serotoninergic transmission

<400> SEQUENCE: 4

Leu Ser Ala Leu Gly Gly Gly Tyr
  1               5
```